(12) United States Patent
Delogé et al.

(10) Patent No.: US 7,611,513 B2
(45) Date of Patent: Nov. 3, 2009

(54) GREATER TROCHANTERIC RE-ATTACHMENT DEVICE

(75) Inventors: Nicolas Delogé, Douvres (FR); Arnaud Aux Epaules, Saint-aubin-sur-mer (FR); Gérard Asencio, Nimes (FR)

(73) Assignee: Benoist Girard SAS (FR)

( * ) Notice: Subject to any disclaimer, the term of this patent is extended or adjusted under 35 U.S.C. 154(b) by 591 days.

(21) Appl. No.: 10/813,213

(22) Filed: Mar. 30, 2004

(65) Prior Publication Data

US 2004/0236337 A1  Nov. 25, 2004

(30) Foreign Application Priority Data

Apr. 2, 2003  (GB)  ................... 0307648.6

(51) Int. Cl.
*A61B 17/82* (2006.01)
(52) U.S. Cl. ....................................................... 606/74
(58) Field of Classification Search ............. 606/74, 606/65, 69–72, 75; 623/23.15, 23.26, 23.27, 623/23.35, 23.42
See application file for complete search history.

(56) References Cited

U.S. PATENT DOCUMENTS

| | | | |
|---|---|---|---|
| 3,824,995 A * | 7/1974 | Getscher et al. ............... 606/69 |
| 3,843,975 A * | 10/1974 | Tronzo .................... 623/23.27 |
| 4,119,091 A | 10/1978 | Partridge |
| 4,153,953 A * | 5/1979 | Grobbelaar ............. 623/23.27 |
| 4,269,180 A | 5/1981 | Dall et al. |
| 4,565,193 A | 1/1986 | Streli |
| 4,651,724 A | 3/1987 | Berentey et al. |
| 4,973,332 A | 11/1990 | Kummer |
| 4,988,350 A | 1/1991 | Herzberg |
| 5,015,248 A | 5/1991 | Burstein et al. |
| 5,163,961 A * | 11/1992 | Harwin .................... 623/22.46 |
| 5,190,545 A | 3/1993 | Corsi et al. |
| 5,462,547 A | 10/1995 | Weigum |
| 5,484,439 A | 1/1996 | Olson et al. |
| 5,665,089 A | 9/1997 | Dall et al. |
| 5,749,872 A | 5/1998 | Kyle et al. |
| 5,797,916 A * | 8/1998 | McDowell .................... 606/74 |
| 5,810,822 A | 9/1998 | Mortier |
| 5,827,286 A | 10/1998 | Incavo et al. |
| 5,941,881 A * | 8/1999 | Barnes ....................... 606/71 |
| 5,973,223 A | 10/1999 | Tellman et al. |
| 6,066,141 A | 5/2000 | Dall et al. |
| 6,183,474 B1 | 2/2001 | Bramlet et al. |
| 6,183,475 B1 | 2/2001 | Lester et al. |

(Continued)

FOREIGN PATENT DOCUMENTS

EP  0 847 730 A  6/1998

(Continued)

*Primary Examiner*—Eduardo C Robert
*Assistant Examiner*—David Comstock
(74) *Attorney, Agent, or Firm*—Lerner, David, Littenberg, Krumholz & Mentlik, LLP

(57) ABSTRACT

A greater trochanter re-attachment device for use in transfemoral revision surgery which comprises a bracket adapted to be attached to a femoral prosthesis with which it is to be used. The bracket has adjustable clamping elements adapted to extend from the brackets and pass around the segment of bone containing the greater trochanter and which when secured in position holds the greater trochanter in position in relation to the femoral prosthesis.

18 Claims, 5 Drawing Sheets

U.S. PATENT DOCUMENTS

| | | |
|---|---|---|
| 6,338,734 B1 | 1/2002 | Burke et al. |
| 6,503,281 B1 | 1/2003 | Mallory |
| 6,695,844 B2 | 2/2004 | Bramlet et al. |
| 7,207,993 B1 * | 4/2007 | Baldwin et al. ............... 606/70 |
| 7,229,445 B2 | 6/2007 | Hayeck et al. |
| 2005/0010226 A1 | 1/2005 | Grady et al. |
| 2006/0217722 A1 | 9/2006 | Dutoit et al. |

FOREIGN PATENT DOCUMENTS

| | | |
|---|---|---|
| EP | 0 955 013 A | 11/1999 |
| FR | 1 493 247 A | 8/1967 |
| FR | 2 792 823 A | 11/2000 |

\* cited by examiner

GREATER TROCHANTERIC RE-ATTACHMENT DEVICE

BACKGROUND OF THE INVENTION

This invention relates to a greater trochanter re-attachment device for use in transfemoral revision surgery. In the surgical technique which involves transfemoral osteotomy the femur is exposed along a proximal/distal line, the soft tissue (skin, muscle) being folded back on each side to expose the bone. The proximal end of the femur is now opened as a "window" and a femoral prosthesis is inserted into the bone canal. Such a surgery is discussed in co-pending U.S. application Ser. Nos. 10/011,047 and 10/008,336 and assigned to the assignee of the present invention, the teachings of which are incorporated herein by reference.

As used herein, when referring to bones or other parts of the body, the term "proximal" means closer to the heart and the term "distal" means more distant from the heart. The term "inferior" means toward the feet and the term "superior" means towards the head. The term "anterior" means towards the front part of the body or the face and the term "posterior" means towards the back of the body. The term "medial" means toward the midline of the body and the term "lateral" means away from the midline of the body.

When this surgery is performed in the transfemoral approach the lengthwise dissection of the bone leaves the greater trochanter in place on a displaced portion of the bone. When the bone is closed again and the greater trochanter is in its correct position there is a loading on the closed bone where it has previously been opened and in known techniques the portions of the bone are wired together thus re-attaching the greater trochanter to the stem. This osteosynthesis occurs at the end of the operation. This is a critical aspect of the surgery because if the flap of bone containing the greater trochanter (the greater trochanter window) is not well attached the stresses on the stem will not be well distributed and a peak of stress can affect the distal tip of the stem leading to a cortex reaction, or a breakage of the stem, or of the screws if the stem is distally fixed.

SUMMARY OF THE INVENTION

The present invention is intended to provide a trochanter re-attachment device and a femoral prosthesis to use the device in combination therewith which will simplify the osteosynthesis and shorten the time required to perform it.

According to the present invention a greater trochanter re-attachment device, such as a flexible bracket, for use in transfemoral revision surgery comprises an attachment device, such as a threaded screw adapted for securing to a femoral prosthesis with which it is to be used. The attachment device carries an adjustable securing element adapted to extend from the attachment device and pass around the flap of a bone segment containing the greater trochanter and which, when secured in position, holds the greater trochanter in position in relation to the femoral prosthesis.

The attachment device may comprise a threaded screw adapted for insertion in a threaded bore or socket in the shoulder of the femoral prosthesis with which it is to be used. The adjustable securing element is preferably in the form of an elongated flexible tie, for example a wire, such as a cerclage wire, strap or ribbon, and two or more ties can be provided if required.

In one preferred embodiment, the threaded screw is provided with openings to receive the elongated flexible tie. In another embodiment, the adjustable securing element is carried on one free end of a bracket which extends over the proximal external surface of the greater trochanter and the other end of which carries the attachment device. With this construction the bracket can have two sections which extend substantially normal to each other, the bracket first section having a curved re-entrant shape to extend around and over the proximal end of the greater trochanter and having a bifurcated free end provided with the adjustable securing element, and the second arm carries the attachment device. The bifurcated free ends of the first arm can each include a guide or guides to locate the adjustable securing element.

The bracket can be made from any convenient material, for example, a synthetic plastics material or metal which is compatible with the requirements of the human body.

The invention also includes a device as set forth above in combination with a femoral prosthesis. Thus, the femoral prosthesis can be provided with a screw threaded socket in its shoulder which is adapted to receive a stem impactor or extractor, or a targeting device, and which also receives the attachment device.

BRIEF DESCRIPTION OF THE DRAWINGS

The invention can be performed in various ways but two embodiments and a description of a previously known method of attaching the greater trochanter during transfemoral revision surgery will now be described by way of example and with reference to the accompanying drawings in which.

DETAILED DESCRIPTION

Figure 1:
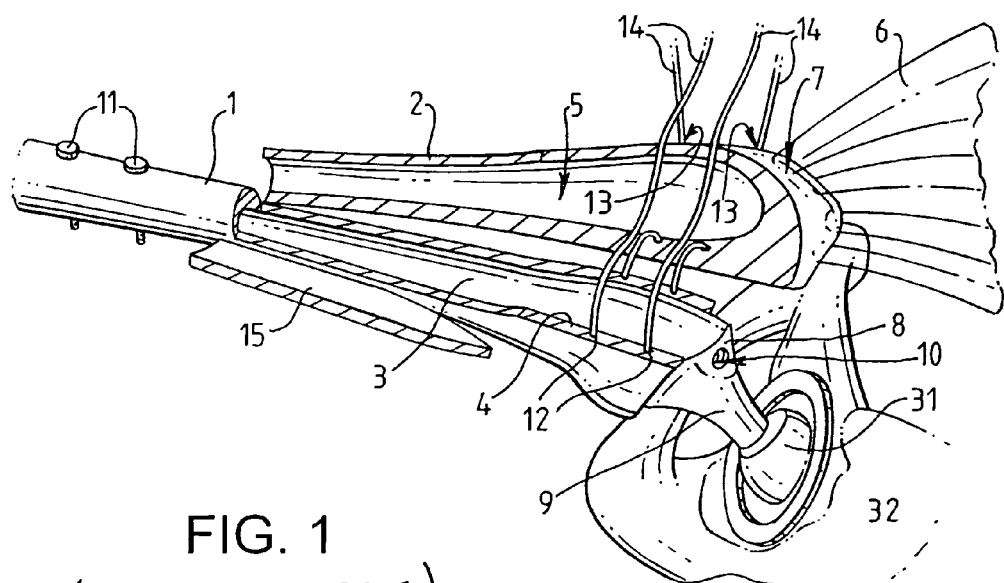
FIG. 1 is a pictorial view showing a known method of attaching the part of the bone of the femur which carries the greater trochanter in the opened (window) position and ready for re-attachment after transfemoral revision surgery.

Referring to FIG. 1 there is shown a known standard technique for closing the greater trochanter window after the installation of a femoral prosthesis. Shaft 1 of the femur has been resected with three cuts along the axis of the bone and a distal transverse cut so that it can be opened, the portion of the proximal femur bone containing the greater trochanter being indicated by reference numeral 2. The femoral prosthesis 3 has been inserted into one part 4 of the bone canal and another part of the canal which is within portion 2 is indicated by reference numeral 5. The third central portion 15 of the bone is also provided which assists when the "window" is closed. Reference numeral 6 indicates the muscles which are attached to the greater trochanter 7.

Femoral prosthesis 3 has a shoulder 8, a neck 9 and a screw threaded bore 10 which is provided in the shoulder 8 to receive a stem impactor or extractor, or a targeting device. The distal end of the prosthesis is located in the bone canal 4 by means of screws 11.

During the surgery holes 12, 13 are drilled through the bone to accept binding wires 14 and when the "window" is closed these binding wires are pulled tight and clamped together.

Figure 5:
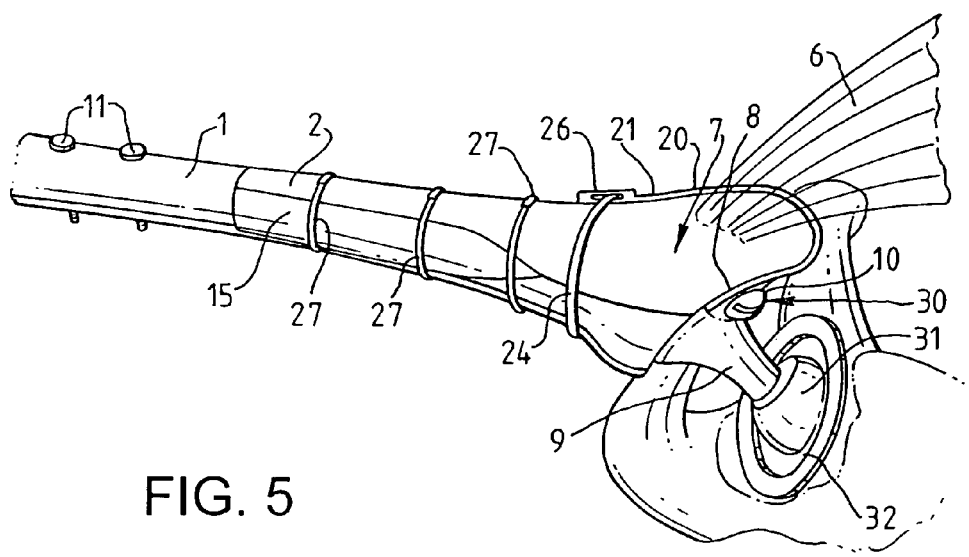
FIG. 5 is a pictorial view of a femur with an installed femoral prosthesis after transfemoral revision surgery and showing the re-attachment device as shown in FIGS. 2, 3 and 4 in place.

Extra tie wires, not shown in FIG. 1 but shown in FIG. 5 are also usually employed to hold the bone together. It will be appreciated that there are difficulties drilling holes 12, 13 in threading the wires through them and then substantially clamping them.

Figure 2:
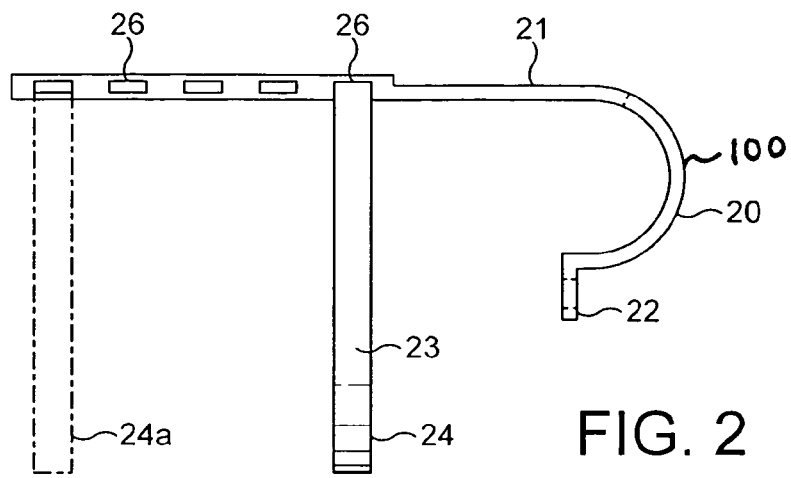
FIG. 2 is a side elevation view of a first embodiment of the greater trochanter re-attachment device according to the present invention.
Figure 3:
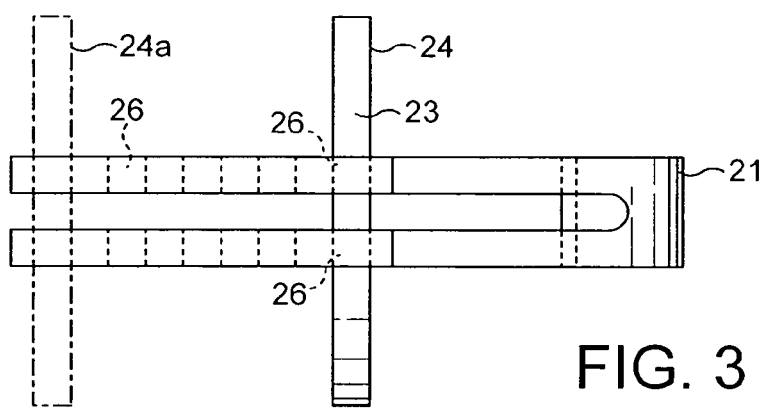
FIG. 3 is plan view of the device shown in FIG. 2.
Figure 4:
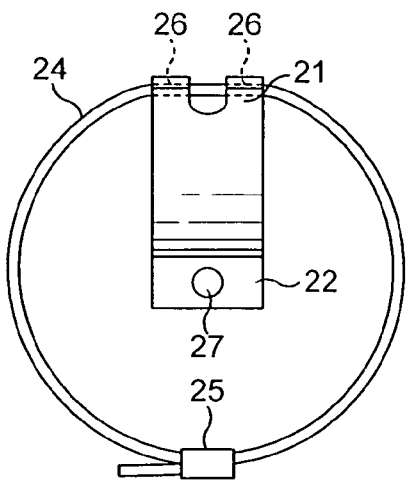
FIG. 4 is an end view of the device shown in FIGS. 2 and 3.

The preferred greater trochanter re-attachment device for use in transfemoral revision surgery according to the present invention is shown in FIGS. 2, 3 and 4 and comprises a bracket 20 which has a first section 21 which is substantially normal to a second section 22. The first section 21 has a curved re-entrant shaped section 100 to extend around and over the proximal end of a greater trochanter. In the preferred embodiment, the free end of section 21 is bifurcated to form a pair of arms, as is most clearly shown in FIGS. 3 and 5, and has adjustable securing element 23 which extend around the external surface of the bone substantially perpendicular to its proximal distal length. In the preferred embodiment, the securing element is in the form of an elongated flexible tie or band 24 which can be, for example, a wire, strap or ribbon. In the drawings, it is shown in ribbon form with an end connector 25. The flexible connector extends through a guide in the bifurcated ends of section 21. In the arrangement shown in the drawings the guides are in the form of rectangular apertures 26 but they could be in the form of clips or grooves on the outer surface of the bifurcated arm or any other convenient construction. As shown in FIGS. 2, 3 and 4 a series of spaced apertures 26 are provided and band 24 can be used in any one of them. If appropriate, one or more further bands, indicated by broken lines 24a can be included. If only one tie is used, or two close together, the unneeded bifurcated arms 2 can be removed.

The second section 22 is provided with an opening 27 to receive an attachment element preferably in the form of a threaded screw 30 for securing to the femoral prosthesis (not shown in FIGS. 2, 3 or 4 but indicated in FIG. 5). Screw 30 thus supports the adjustable securing band 24 via bracket 20.

FIG. 5 shows how the device shown in FIGS. 2, 3 and 4 is employed to re-attach the greater trochanter after transfemoral revision surgery.

Bracket 20 is first placed in position on greater trochanter 7, the bifurcated arms of section 21 enabling the surgeon to pass them through the muscles 6 until the bracket is in position shown in FIG. 5. In this position the opening 27 in the second section 22 is aligned with threaded bore 10 in the prosthesis and a screw 30 is used as an attachment element to secure bracket 20 to shoulder 8 of prosthesis 3.

Flexible tie 24 can now be passed through the apertures 26, assembled around the bone as shown in FIG. 5 and tightened so that it acts as securing device extending around the external surface of the bone substantially normal to its proximal/distal length. If desired the flexible band 24 could be pre-assembled on the end of section 21 prior to connecting the bracket to shoulder 8 of prosthesis 3.

Figure 6:
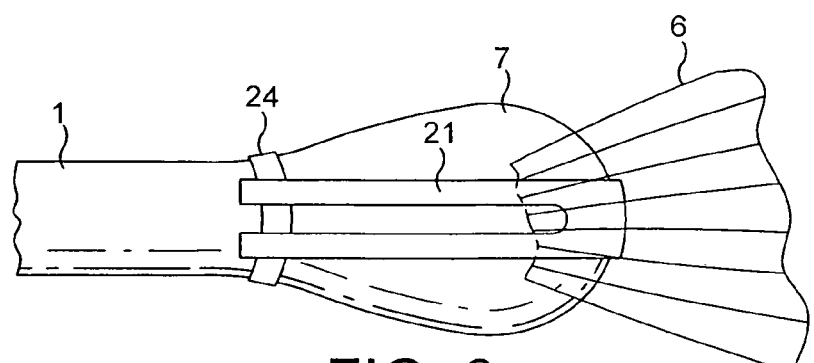
FIG. 6 is a pictorial plan view of the greater trochanter shown in FIG. 5 with the re-attachment device in place.

In the assembly shown in FIGS. 5 and 6, a single band 24 is used in a single aperture 26 in the bifurcated arms of bracket section 21 but if required a bracket having a number of apertures 26 could be employed with two or more ties or bands 24a.

Additional external wires 27 can also be provided to hold portion 2, part 4 and central portion 15 of the bone in place. It will be appreciated that the present invention provides a simple device for rigidly holding the greater trochanter in place after the femoral prosthesis has been inserted.

FIGS. 1 and 5 show head 31 of the prosthesis in place in an acetabular cup 32. The technique of being able to place the head 31 in position during transfemoral revision surgery is one of the advantages of the present invention.

Figure 7:
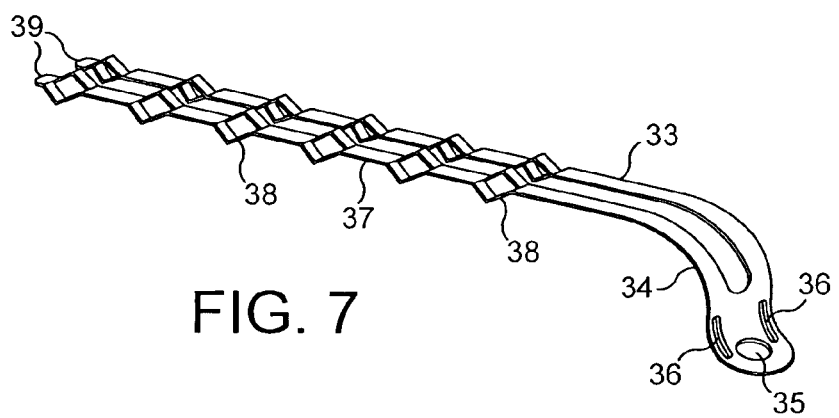
FIG. 7 is a top isometric view of a second embodiment according to the present invention.
Figure 8:
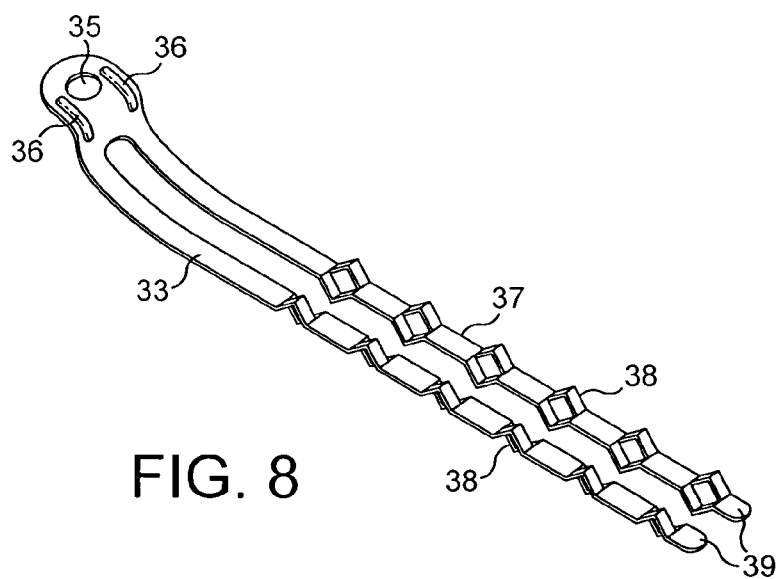
FIG. 8 is a bottom isometric view of that second embodiment similar to that shown in FIG. 7.

FIGS. 7 and 8 show an alternative construction for bracket 20 and the same reference numerals are used to indicate similar parts to those shown in FIGS. 2 to 4. With this construction, the bracket is indicated by reference numeral 33 and is made from a resilient material, for example a resilient or bendable metal strip. The bracket is initially formed with a single curve 34 which replaces the curved re-entrant shape shown in FIGS. 2 to 4. This end of the bracket has an opening 35 to receive the threaded screw 30 and the part of the bracket adjacent opening 35 is again curved and passed with troughs 36 to reinforce it.

The first section 37 is again bifurcated and is split and dimpled on each side to provide a series of transversely extending openings 38 in each of the bifurcated arms 39.

In the preferred embodiment, the bracket is formed by a single pressing or stamping which provides the troughs 36 and the slits to allow the dimples to be produced.

It will be seen from the drawing that section 37 of the bracket shown in FIGS. 7 and 8 is somewhat longer than section 21 shown in FIGS. 2, 3 and 4. In use, the bracket shown in FIGS. 7 and 8 is first attached to the prosthesis by the threaded screw 30. In this position, section 37 will extend upwardly away from the bone at the greater trochanter 7. The surgeon can now however bend the bracket to provide a close and accurate fit due to the bracket's resilience. An elongated flexible tie 24 as shown in FIGS. 2, 3 and 4, can now be located through the appropriate openings 38 to hold the bracket in place on the greater trochanter 7. If desired a further elongated flexible tie 24a can be used as described with regard to FIGS. 2, 3 and 4.

FIGS. 9 and 10, 11 and 12 shown other embodiments of a greater trochanter re-attachment device for use in transfemoral revision surgery according to the invention. The same reference numerals are used to indicate similar parts to those shown in FIGS. 1 to 6.

Figure 9:
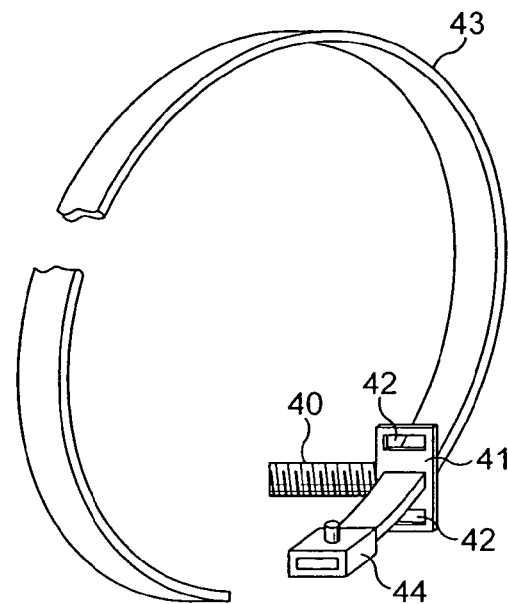
FIG. 9 is a pictorial side view of a third embodiment of the present invention.

In the embodiment of FIG. 9, the attachment device is provided by a threaded screw 40 which has a cylindrical head 41. A series of rectangular openings 42 extend diametrically across the head. The adjustable securing means is again provided by an elongated tie 43 having a connector 44. Although a flexible tie is shown a wire or similar element could be employed.

Figure 10:
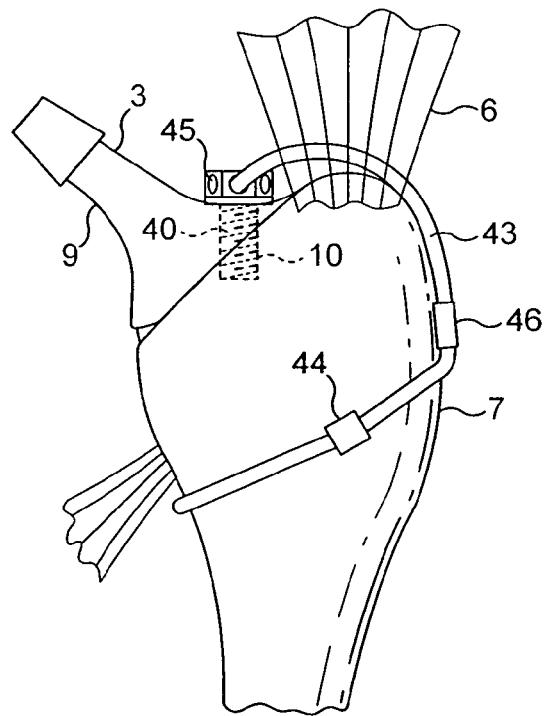
FIG. 10 is a pictorial side view of a fourth embodiment of the invention on a femur.
Figure 11:
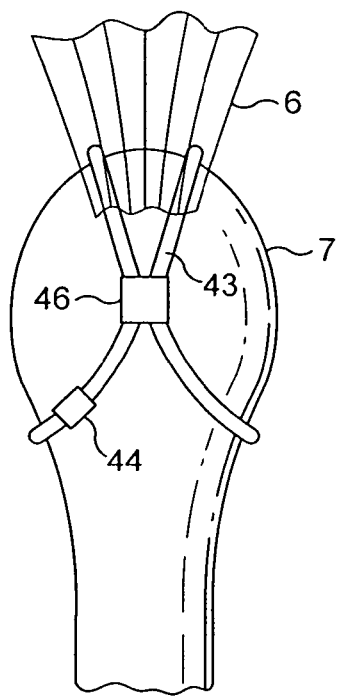
FIG. 11 is a pictorial front view of the assembly shown in FIG. 10.
Figure 12:
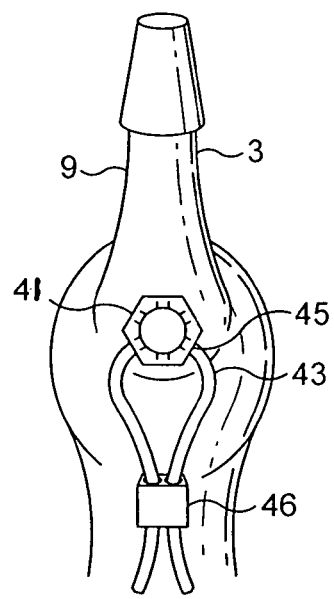
FIG. 12 is a pictorial top view of the assembly shown in FIGS. 10 and 11.

FIGS. 10, 11 and 12 show a device similar to that shown in FIG. 9 but employing a flexible wire which can pass through circular openings 45 in head 41 of the screw. The device is employed to re-attach the greater trochanter 2 after transfemoral revision surgery but in order to clarify the drawings various integers shown in FIGS. 1 and 5 are omitted. Screw 40 is located in the screw threaded socket 10 in the prosthesis and the flexible tie 43 is first threaded through a sleeve 46 and then through one of the openings 45 with the connector 44 to one side. The tie is now passed around the greater trochanter 2 and back through the sleeve 46, around the end of the central portion 15 of the bone and back through the connector 44. The tie is then pulled tight so that the greater trochanter is held in the position shown in FIG. 5 so that it acts as a securing means extending around the external surface of the greater trochanter 2 and the bone portion 15 to hold them in position, the free end protruding from the connector 44 is then removed.

Alternative wrapping arrangements for tie 43 can be used as desired by the surgeon provided that the greater trochanter and portion of the bone 15 are held tightly in position.

It will be appreciate that with this arrangement the device is simple to operate but can provide the necessary pressure.

Additional external wires 29 can be used to hold portion 2, part 4 and central portion 15 of the bone in place as described with regard to FIGS. 1 to 8 and the band 43 has the ability of being able to pass through muscles 6 without disadvantage.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A greater trochanter re-attachment device for use in transfemoral revision surgery comprising an attachment means adapted for securing the device to a proximal end of a femoral prosthesis with which it is to be used, a bracket having a first portion for extending distally along the femur and an adjustable securing means adapted to extend through a guide on the first portion of the bracket and around a flap of bone containing the greater trochanter and which securing means, when secured in position, holds the greater trochanter in position in relation to the femoral prosthesis wherein the guide consists of a multiplicity of slits through the first portion spaced at intervals therealong intermediate first and second sides of the first portion and multiplicity of outwardly extending sections deformed outwardly of a bone surface on the first side of each slit along the bracket first portion, each of the outwardly extending sections of the bracket first portion extending away from a bone contacting surface of the bracket, the securing means extending below the outwardly extending section and above a bone contacting section of the first portion on the second side of the slits.

2. The greater trochanter re-attachment device as set forth in claim 1 wherein the attachment means comprises a threaded screw adapted for insertion in a screw threaded socket in a proximal shoulder of the femoral prosthesis with which it is to be used.

3. The greater trochanter re-attachment device as set forth in claim 1 wherein said adjustable securing means are in the form of one or more elongated flexible ties.

4. The greater trochanter re-attachment device as set forth in claim 3 wherein the elongated flexible tie is in the form of a wire or ribbon.

5. The greater trochanter re-attachment device as set forth in claim 1 wherein the bracket has a second portion which when in use extends over the proximal external surface of the greater trochanter.

6. The greater trochanter re-attachment device as set forth in claim 5 wherein the first bracket portion has two arms which are substantially parallel to each other, each arm having a curved re-entrant shape forming the second bracket portion for extending over a proximal end of the greater trochanter and having a bifurcated free end provided with said adjustable securing means.

7. The greater trochanter re-attachment device as set forth in claim 6 wherein the bifurcated free ends of each arm include the guide for the adjustable securing means.

8. The greater trochanter re-attachment device as set forth in claim 7 wherein the bracket is made from a synthetic plastics material or metal which is compatible with the requirements of the human body.

9. The greater trochanter re-attachment device as set forth in claim 8 wherein the bracket is made from a resilient material which can be deformed to fit the bracket to the shape of the greater trochanter with which it is used.

10. The greater trochanter re-attachment device as set forth in claim 1 in combination with a femoral prosthesis.

11. The greater trochanter re-attachment device as set forth in claim 10 wherein the femoral prosthesis is provided with a threaded bore in a proximal shoulder for receiving the attachment means.

12. A device for securing bone segments of a proximal femur after implantation of a prosthetic femoral component, comprising:
a bracket for engaging a bone segment of the proximal femur, the bracket including at least one arm extending distally along an outer surface of the femur, the arm including a guide;
a securing element for securing said bracket to a femoral component extending through the guide;
at least one band having first and second ends extending through the guide in said arm in a circumferential direction around the femur wherein the guide consists of a multiplicity of slits through the arm spaced at intervals thereon intermediate first and second sides of the arm, the slits spaced by flat bone-contacting sections and a multiplicity of outwardly extending sections of the at least one arm, the outwardly extending section of the at least one arm extending away from a bone contacting surface, the band extending below the outwardly extending section and above a bone contacting section of the arm on the second side of the slits; and
a clamp for joining said first and second ends of said band and preventing relative movement therebetween.

13. The device as set forth in claim 12 wherein said bracket includes two spaced apart arms extending distally along the outer surface of the femur.

14. The device as set forth in claim 13 wherein said arms extend generally parallel to a longitudinal axis of the femur and said guide extending generally perpendicular thereto.

15. The device as set forth in claim 12 wherein the femoral component includes a threaded bore and the bracket has an opening alignable with said threaded bore.

16. The device as set forth in claim 15 wherein the securing element is a threaded bolt insertable through said opening in the bracket into said threaded bore.

17. A system for clamping bone segments of a resected proximal femur around a femoral component comprising:
a femoral component having a stem extending along a longitudinal axis and having a threaded bore at a proximal end thereof;
a bracket for engaging a bone segment of the proximal femur, the bracket including a pair of generally parallel arms extending from an attachment portion;
a threaded coupling element for coupling the attachment portion of the bracket to the threaded bore of the femoral component; and
at least one elongated clamping element for extending circumferentially around the femur in a direction transverse to said longitudinal axis after said bracket engages said bone segment to clamp said bone segments around the femoral component wherein each generally parallel arm has a guide therein for receiving the at least one elongated clamping element wherein the guide consists of a multiplicity of slits spaced at intervals through each arm located intermediate first and second sides thereof and the slits spaced by flat bone-contacting sections, a multiplicity of outwardly extending sections deformed away from a bone surface on the first side of each slit of each arm each extending away from a bone contacting surface of the bracket, the elongated clamping element extending below the outwardly extending section of each arm and above a bone contacting section of each arm on the second side of each slit.

18. The system as set forth in claim 17 wherein the bracket has a portion with a curved re-entrant shape for extending over a proximal end of the greater trochanter.

* * * * *